United States Patent [19]

Marhold

[11] Patent Number: 4,681,955
[45] Date of Patent: Jul. 21, 1987

[54] BENZO-FUSED FLUORINATED HETEROCYCLIC COMPOUNDS AND A PROCESS FOR THEIR PREPARATION

[75] Inventor: Albrecht Marhold, Leverkusen, Fed. Rep. of Germany

[73] Assignee: Bayer Aktiengesellschaft, Leverkusen, Fed. Rep. of Germany

[21] Appl. No.: 762,984

[22] Filed: Aug. 6, 1985

[30] Foreign Application Priority Data

Aug. 24, 1984 [DE] Fed. Rep. of Germany ....... 3431222

[51] Int. Cl.$^4$ .................. C07D 319/20; C07D 319/22
[52] U.S. Cl. .................................. 549/362; 549/274; 549/359; 549/366
[58] Field of Search ................ 549/362, 366, 274, 359

[56] References Cited

U.S. PATENT DOCUMENTS 4,264,456  4/1981  Sprecker et al. ................ 549/274
4,405,639  9/1983  Fuchs et al. .................... 549/362

FOREIGN PATENT DOCUMENTS 0041131 12/1981 European Pat. Off. .

OTHER PUBLICATIONS

The Journal of the American Chemical Society, vol. LXXVII, 1955, pp. 1136–1138.

*Primary Examiner*—Dolph H. Torrence
*Attorney, Agent, or Firm*—Sprung, Horn, Kramer & Woods

[57] ABSTRACT

New compounds of the formula

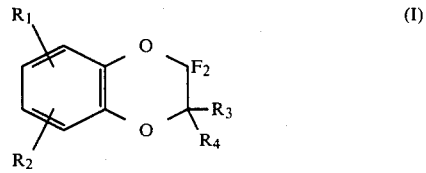

(I)

a process for their preparation and their use as intermediates for insecticides.

13 Claims, No Drawings

BENZO-FUSED FLUORINATED HETEROCYCLIC COMPOUNDS AND A PROCESS FOR THEIR PREPARATION

The present invention relates to new benzo-fused fluorinated heterocyclic compounds of the formula

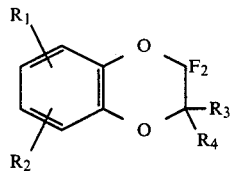
(I)

in which $R_1$ and $R_2$ independently of one another represent H, F, Cl, Br, COF, COCl, CO-O-alkyl, CN, alkyl, $NO_2$, $SO_2F$, $SO_2Cl$, $OCF_3$, $OCF_2Cl$, $SCF_3$, $CF_3$, $SCF_2Cl$, phenyl, substituted phenyl, O-alkyl, O-aryl, S-alkyl or S-aryl, or $R_1$ and $R_2$ together represent

, $R_3$ represents H, alkyl, aryl, CO-O-alkyl, CN, substituted alkyl or substituted aryl and $R_4$ represents alkyl, aryl, CO-O-alkyl, CN, substituted alkyl or substituted aryl.

If $R_1$, $R_2$, $R_3$ and/or $R_4$ in formula (I) represents CO-O-alkyl, alkyl, O-alkyl, S-alkyl and/or substituted alkyl, the particular alkyl radical can contain, for example, 1 to 6 C atoms. Such an alkyl radical preferably contains 1 to 4 C atoms.

If $R_1$, $R_2$, $R_3$ and/or $R_4$ in formula (I) represents O-aryl, S-aryl, aryl and/or substituted aryl, the particular aryl radical can contain, for example, 6 to 10 C atoms. The particular aryl radical is preferably a phenyl radical.

If $R_1$, $R_2$, $R_3$ and/or $R_4$ in formula (I) represents substituted phenyl, substituted alkyl and/or substituted aryl, examples of substituents which can be present are $NO_2$, F, Cl, Br, CN, $C_1$- to $C_4$-alkyl, $SO_2Cl$, $SO_2F$, $OCF_3$, $OCF_2H$, $CF_2Cl$, $SCF_3$, $SCF_2H$, $CF_3$, O-$C_1$- to $C_4$-alkyl or S-$C_1$- to $C_4$-alkyl.

Preferably, in formula (I), $R_1$ and $R_2$ independently of one another represent H, F, Cl, $CH_3$, $NO_2$, CO-O-$C_1$- to $C_4$-alkyl, COCl or phenyl, or $R_1$ and $R_2$ together represent

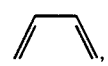, $R_3$ represents H, $C_1$- to $C_4$-alkyl, CO-O-$C_1$-$C_4$-alkyl, CN or phenyl and $R_4$ represents $C_1$- to $C_4$-alkyl or phenyl.

Particularly preferably, in formula (I), $R_1$ represents H and $R_2$ represents H, $NO_2$, $CH_3$, CO—O—$C_1$— to $C_4$-alkyl, COCl or phenyl, or $R_1$ and $R_2$ together represent

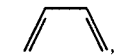, $R_3$ represents H, $CH_3$, CO—O—$CH_3$, CN or phenyl and $R_4$ represents $CH_3$ or phenyl.

The process according to the invention for the preparation of the new chemical compounds of the formula (I)

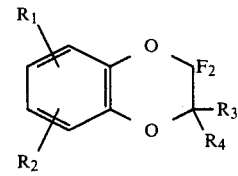
(I)

in which $R_1$ and $R_2$ independently of one another represent H, F, Cl, Br, COF, COCl, CO-O-alkyl, CN, alkyl, $NO_2$, $SO_2Cl$, $OCF_3$, $OCF_2Cl$, $SCF_3$, $CF_3$, $SCF_2Cl$, phenyl, substituted phenyl, O-alkyl, O-aryl, S-alkyl or S-aryl, or $R_1$ and $R_2$ together represent

, $R_3$ represents H, alkyl, aryl, CO-O-alkyl, CN, substituted alkyl or substituted aryl and $R_4$ represents alkyl, aryl, CO-O-alkyl, CN, substituted alkyl or substituted aryl.

is characterised in that (a) pyrocatechol or a pyrocatechol derivative of the formula (II)

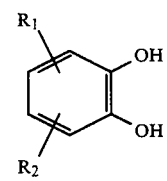
(II)

in which $R_1$ and $R_2$ have the abovementioned meaning, is reacted with compounds of the formula (III)

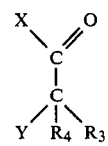
(III)

in which $R_3$ and $R_4$ have the abovementioned meaning,

X represents halogen, O-alkyl, S-alkyl or hydroxy and

Y represents halogen, in the presence of a solvent and with the addition of a condensing agent, to give compounds of the formula (IV)

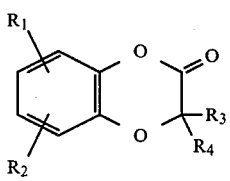

in which $R_1$, $R_2$, $R_3$ and $R_4$ have the abovementioned meaning, (b) the compounds of the formula (IV) are reacted at elevated temperature with at least an equimolar amount of phosphorus pentachloride to give compounds of the formula (V)

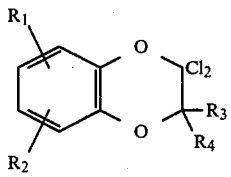

in which $R_1$, $R_2$, $R_3$ and $R_4$ have the abovementioned meaning, and (c) the compounds of the formula (V) are reacted with a fluorinating agent to give compounds of the formula (I).

Compounds of the formula (II) in which $R_1$ and $R_2$ independently of one another represent H, F, Cl, $CH_3$, $NO_2$, CO—O—$C_1$— to $C_4$-alkyl, COCl or phenyl or $R_1$ and $R_2$ together represent

are preferably employed in the process according to the invention. Compounds of the formula (II) in which $R_1$ represents H and $R_2$ represents H, $CH_3$, $NO_2$, CO—O—$C_1$— to $C_4$-alkyl, COCl or phenyl, or $R_1$ and $R_2$ together represent

are particularly preferred.

If X in formula (III) represent halogen, F, Cl and Br are preferred, in particular Cl and Br. If X in formula (III) represents O-alkyl or S-alkyl, the particular alkyl radical can contain, for example, 1 to 4 C atoms. Methyl radicals are preferred. Y in formula (III) preferably represents Cl or Br.

In formula (III), $R_3$ preferably represents H, $C_1$- to $C_4$-alkyl, CO—O—$C_1$— to $C_4$-alkyl, CN or phenyl and $R_4$ preferably represents $C_1$- to $C_4$-alkyl or phenyl. Particularly preferably, $R_3$ represents H, $CH_3$, CO—O—$CH_3$, CN or phenyl and $R_4$ represents $CH_3$ or phenyl.

The compounds of the formula (II) are either commercial products or are accessible in a simple manner, for example according to Houben-Weyl, Methoden der organischen Chemie (Methods of Organic Chemistry), Volume VI/1c, page 327 (1976) or in a manner analogous thereto.

The compounds of the formula (III) are either commercial products or are accessible in a simple manner, for example according to U.S. Pat. No. 2,778,851, or in a manner analogous thereto.

1 to 1.5 moles of a compound of the formula (III), for example, can be employed per mole of a compound of the formula (II). Preferably, 1 to 1.2 moles of a compound of the formula (III) are employed per mole of a compound of the formula (II).

Reaction step (a) is carried out in the presence of a solvent and with the addition of a condensing agent. Examples of suitable solvents are water, alcohols, for example those with 1 to 4 C atoms, acetonitrile, dimethylformamide or mixtures thereof. Examples of suitable condensing agents are basic compounds, such as alkali metal or alkaline earth metal hydroxides, alkali metal or alkaline earth metal carbonates or amines, such as pyridine and N,N-dimethylaniline, or mixtures thereof. The condensing agent can be employed, for example, in amounts of 1 to 3 moles per mole of the compound of the formula (III). Condensing agent amounts of 1 to 2 moles per mole of the compound of the formula (III) are preferred.

Reaction step (a) can be carried out, for example, at 20° to 150° C. Preferred temperatures are those from 20° to 140° C.

The compounds of the formula (IV) can be obtained from the reaction mixture present after reaction step (a) in a manner which is known per se, for example by extraction, distillation and/or crystallisation.

In reaction step (b), the compounds of the formula (IV) are reacted at elevated temperature with at least an equimolar amount of phosphorus pentachloride. Examples of suitable temperatures are those in the range from 50° to 240° C. The reaction is preferably carried out at 60° to 220° C., particularly preferably at 60° to 200° C.

In general, larger excesses of phosphorus pentachloride present no problems. For economic reasons, 1 to 1.5 moles of phosphorus pentachloride are preferably added per mole of a compound of the formula (IV). The phosphorus pentachloride can also be formed in situ, for example from phosphorus trichloride and elemental chlorine.

In general, it is advantageous to add the phosphorus pentachloride in several part amounts in succession. A procedure can be followed, for example, in which only 0.1 to 0.3 mole of phosphorus pentachloride is initially added per mole of a compound of the formula (IV) and the remaining phosphorus pentachloride is added only after the reaction which begins has subsided. However, it is also possible to take the entire amount of phosphorus pentachloride to be employed and to add the compound of the formula (IV) in portions.

The presence of solvents in reaction step (b) is not absolutely necessary, but in many cases it is advantageous, for example for improving the stirrability and/or the removal of heat. Examples of suitable solvents are chlorinated hydrocarbons, in particular those with higher boiling points, such as carbon tetrachloride, chlorobenzene and dichlorobenzene. However, phosphorus oxychloride is preferably employed as the solvent, since this is also formed during the reaction, from the phosphorus pentachloride employed, and no particular expenditure is required for removal of this product.

The reaction in reaction step (b) has in general ended within 2 to 3 hours at temperatures from 60° to 200° C. At lower (higher) temperatures, longer (shorter) reaction times may be advantageous. Longer reaction times also in general do not have an adverse effect if excess phosphorus pentachloride is employed.

The compounds of the formula (V) obtained in reaction step (b) can be isolated in a manner which is known per se, for example by extraction, distillation and/or crystallisation. However, it is not absolutely necessary to isolate the compounds of the formula (V).

In reaction step (c), compounds of the formula (V) are reacted with a fluorinating agent. Examples of suitable fluorinating agents are hydrogen fluoride, antimony trifluoride potassium fluoride and sodium fluoride. Hydrogen fluoride is preferably used.

The fluorinating agent can be employed, for example, in amounts of 2 to 15 moles per mole of a compound of the formula (V). This amount is preferably 3 to 6 moles per mole of a compound of the formula (V).

Reaction step (c) can be carried out, for example, at temperatures from $-10°$ to $120°$ C. if hydrogen fluoride is employed as the fluorinating agent. In other cases, this temperature can also be higher, and can be, for example, up to $250°$ C. Temperatures of $0°$ to $80°$ C. are preferred. The pressure in reaction step (c) can be, for example, 1 to 50 bar. It is preferably in the range from 1 to 30 bar. A solvent is not necessary for this reaction step, but it can also be carried out, if appropriate, in the presence of a solvent. Suitable examples for this are dichloromethane, 1,2-dichloroethane, chlorobenzene and dichlorobenzene.

The reaction mixture present after reaction step (c) can be worked up, for example, by fractional distillation. After removal of highly volatile constituents, fractional distillation in vacuo is particularly advantageous for isolating the compounds of the formula (I).

It is decidedly surprising that the new compounds of the formula (I) can be prepared in the manner according to the invention, since it is known, for example from J.A.C.S. 77, 1137 (1955), that although keto groups can be chlorinated with phosphorus pentachloride, ester groups cannot (see formula (IV)). In the reference, for example, it is reported that ethyl β-chloroisocrotonate, ethyl β-chlorocrotonate and unreacted ethyl acetoacetate but not 1-ethoxy-1,1,3,3-tetrachlorobutane were obtained from the reaction of ethyl acetoacetate with phosphorus pentachloride.

The new compounds of the formula (I) are useful intermediates for the preparation of benzoylureas which have insecticidal and/or acaricidal actions. Such benzoylureas can be obtained from the compounds of the formula (I) by introducing, if appropriate, a nitro group by methods which are known per se and then reducing the nitro group present in all cases to an $NH_2$ function and reacting the amines thus obtained with benzoyl isocyanates.

It will be understood that the specification and examples are illustrative but not limitative of the present invention and that other embodiments within the spirit and scope of the invention will suggest themselves to those skilled in the art.

EXAMPLES

Example 1

768 g of chloroacetic acid and 880 g of pyrocatechol were initially introduced into 3,200 ml of water, and a solution of 340 g of NaOH in 1.6 l of water was added dropwise. The mixture was then boiled and stirred under reflux for 4 hours, cooled and acidified with sulphuric acid and the solid product was filtered off with suction. 932 g of benzodioxenone with a boiling point of $124°$ to $125°$ C. under 20 mbar and a melting point of $50°$ to $52°$ C. were obtained by distillation in vacuo.

Example 2

70 g of potassium carbonate and 55 g of pyrocatechol were initially introduced into 250 ml of acetonitrile and the mixture was heated to $50°$ C. 100 g of methyl bromoisobutyrate were then added dropwise and the mixture was boiled and stirred under reflux for 5 hours. After the acetonitrile had been distilled off, 200 ml of water were added to the residue which remained and the mixture was acidified with hydrochloric acid and extracted with methylene chloride. 74 g of 2,2-dimethyl-benzodioxen-3-one with a boiling point of $115°$ to $120°$ C. under 14 mbar and a melting point of $42°$ to $44°$ C. were obtained from the extract by distillation.

Examples 3 to 7

The procedure followed was as in Example 2, but other starting substances were employed. The starting substances and reaction results can be seen from Table 1.

TABLE 1

| Example No. | Starting substance of the formula (II) | Starting substance of the formula (III) | Reaction product | Boiling point (b.p.) and melting point (m.p.) of the reaction product | Yield |
|---|---|---|---|---|---|
| 3 | Pyrocatechol | $CH_3$—CH—$CO_2CH_3$<br>\|<br>Br | $R_3 = CH_3$ $R_4 = H$<br>S, T, U = H | b.p.: 130–135° C./20 mbar<br>m.p.: 46–48° C. | 68% |
| 4 | Pyrocatechol | phenyl-CH—$CO_2C_2H_5$<br>\|<br>Br | $R_3$ = phenyl $R_4 = H$<br>S, T, U = H | b.p.: 120–128° C./0.7 mbar<br>m.p.: 73–75° C. | 82% |
| 5 | Pyrocatechol | $C_2H_5CO_2$—CH—$CO_2C_2H_5$<br>\|<br>Cl | $R_3 = CO_2C_2H_5$ $R_4 = H$<br>S, T, U = H | b.p.: 124° C./19 mbar<br>m.p.: 47–49° C. | 46% |
| 6 | 4-Nitro-pyrocatechol | $CH_3$—CH—$CO_2CH_3$<br>\|<br>Br | $R_3 = CH_3$ $R_4 = H$<br>T = $NO_2$ | b.p.: 170–178° C./0.3 mbar<br>m.p.: | 73% |

TABLE 1-continued

| Example No. | Starting substance of the formula (II) | Starting substance of the formula (III) | Reaction product (with U, T, S positions on benzene ring; R3, R4 on dioxene) | Boiling point (b.p.) and melting point (m.p.) of the reaction product | Yield |
|---|---|---|---|---|---|
| 7 | 3-Methyl-pyrocatechol | CH$_3$—CH(Br)—CO$_2$CH$_3$ | (1) R$_3$, U = CH$_3$, R$_4$ = H, S, T = H  (2) R$_3$, S = CH$_3$, R$_4$ = H, T, U = H  Parts by weight of (1) to (2) = 64 to 36 | b.p.: 135–140° C./18 mbar  m.p.: | 78% |

Example 8

115 g of 2,2-dimethyl-benzodioxen-3-one, obtained according to Example 2, were mixed with 172 g of phosphorus pentachloride and the mixture was heated to the reflux point, with stirring. The mixture became liquid at 65° C. and the reflux temperature was reached at 120° C. After 2 hours, the phosphorus oxychloride formed was distilled off and the crude product was subjected to distillation. 128 g of 2,2-dimethyl-3,3-dichloro-benzodioxene with a boiling point of 132° to 140° C. under 20 mbar and a melting point of 63° to 64° C. (recrystallised from hexane) were obtained.

Examples 9 to 12

The procedure followed was as in Example 8, but other starting substances were employed. The starting substances and the reaction results can be seen from Table 2.

stirring, and the mixture was finally warmed to 20° C. The mixture was stirred until no further evolution of hydrogen chloride was to be observed (about 4 hours). The excess hydrogen fluoride was then distilled off and 83 g of 2,2-dimethyl-3,3-difluoro-benzodioxene with a boiling point of 84° to 86° C. under 22 mbar and a refractive index n$_D^{20}$ of 1.4740 were subsequently obtained.

Example 14

2,000 ml of hydrogen fluoride were initially introduced into a stainless steel apparatus and 1,295 g of 2,2-dimethyl-3,3-dichloro-benzodioxene, obtained according to Example 8 and dissolved in methylene chloride, were added dropwise at −3° C. The mixture was then heated first at 20° C. for 2 hours and then at 60° C. for 1 hour, with stirring. After working up of the reaction mixture as described in Example 13, 831 g of 2,2-dimethyl-3,3-difluoro-benzodioxene were obtained.

TABLE 2

| Example No. | Starting substance of the formula (IV), obtained according to Example No. | Reaction product (S, R$_3$, R$_4$ substituents) | Boiling point (b.p.) and melting point (m.p.) of the reaction product | Yield |
|---|---|---|---|---|
| 9 | 1 | R$_3$, R$_4$, S = H | b.p.: 128–134° C./18 mbar | 82% |
| 10 | 3 | R$_3$ = H, R$_4$ = CH$_3$, S = H | b.p.: 125–130° C./18 mbar  m.p.: 46–48° C. | 86% |
| 11 |  | R$_3$ = H, R$_4$ = H, S = NO$_2$ | m.p.: 32–36° C. |  |
| 12 | 4 | R$_3$ = H, R$_4$ = phenyl, S = H | b.p.: 100–110° C./0.1 mbar | 78% |

Example 13

128 g of 2,2-dimethyl-3,3-dichloro-benzodioxene, obtained according to Example 8, were initially introduced into a stainless steel fluorination apparatus and 250 ml of hydrogen fluoride were metered in at −10° C. The temperature was slowly increased to +10° C., with

Examples 15 to 17

The procedure followed was as in Example 13, but other starting substances were employed. The starting substances and the reaction results can be seen from Table 3.

TABLE 3

| Example No. | Starting substance of the formula (V) obtained according to Example No. | Reaction product (T, R$_3$, R$_4$ substituents) | Boiling point of the reaction product | Refractive index n$_D^{20}$ of the reaction product | Yield |
|---|---|---|---|---|---|
| 15 | 10 | R$_3$ = CH$_3$; R$_4$, T = H | 75–78° C./18, bar | 1.4754 | 55% |
| 16 | 12 | R$_3$ = phemyl; R$_4$ = H; T = H | 140–145° C./8 mbar | 1.5471 | 78% |
| 17 |  | R$_4$ = H; R$_3$ = CH$_3$; T = NO$_2$ | 95–100° C./0.2 mbar | 1.5205 | 81% |
| 18 |  | R$_3$, R$_4$ = CH$_3$; | 118–25° C./0.18 mbar | 1.5145 | 84% |

TABLE 3-continued

| Example No. | Starting substance of the formula (V) obtained according to Example No. | Reaction product (structure with T, O, F$_2$, R$_3$, R$_4$; T = NO$_2$) | Boiling point of the reaction product | Refractive index n$_D^{20}$ of the reaction product | Yield |
|---|---|---|---|---|---|

What is claimed is:

1. A benzo-fused fluorinated heterocyclic compound of the formula (I)

in which

R$_1$ and R$_2$ each independently is H, F, Cl, Br, COF, COCl, CO-O-alkyl, CN, alkyl, NO$_2$, SO$_2$F, SO$_2$Cl, OCF$_3$, OCF$_2$Cl, SCF$_3$, CF$_3$, SCF$_2$Cl, phenyl, substituted phenyl, O-alkyl, O-aryl, S-alkyl or S-aryl, or R$_1$ and R$_2$ together are R$_3$ is alkyl, aryl, CO-O-alkyl, CN, substituted alkyl or substituted aryl, and R$_4$ is alkyl, aryl, CO-O-alkyl, CN, substituted alkyl or substituted aryl.

2. A compound according to claim 1, in which

R$_1$ and R$_2$ each independently is H, F, Cl, CH$_3$, NO$_2$, CO-O-C$_1$- to C$_4$-alkyl, COCL or or phenyl, or R$_1$ and R$_2$ together are R$_3$ is C$_1$- to C$_4$-alkyl, CO-O-C$_1$- to C$_4$-alkyl, CN or phenyl, and R$_4$ is C$_1$- to C$_4$-alkyl or phenyl.

3. A compound according to claim 1, in which R$_1$ and R$_2$ each independently is H, F, Cl, Br, COF, COCl, CO-O-alkyl, CN, NO$_2$, SO$_2$F, SO$_2$Cl, OCF$_3$, OCF$_2$Cl, SCF$_3$, SCF$_2$Cl, phenyl, substituted phenyl, O-alkyl, O-aryl, S-alkyl or R$_1$ and R$_2$ together are 4. A compound according to claim 1, in which R$_1$ and R$_2$ each independently is H, F, NO$_2$, or COF, R$_3$ is CH$_3$ and R$_4$ is CH$_3$, phenyl or t-butyl.

5. A compound according to claim 1, of the formula

6. A process for the preparation of a compound according to claim 1,
which comprises
(a) reacting a pyrocatechol of the formula with a carbonyl-containing compound of the formula in which
X is halogen, O-alkyl, S-alkyl or hydroxy and
Y is halogen,
in the presence of a solvent and with the addition of a condensing agent, to produce a benzodioxenone of the formula (b) reacting the benzodioxenone at elevated temperature with phosphorus pentachloride to produce a dichlorobenzodioxene of the formula and (c) reacting the dichlorobenzodioxene with a fluorinating agent.

7. The process according to claim 6, in which
$R_1$ and $R_2$ each independently is H, F, Cl, $CH_3$, $NO_2$, CO-O-$C_1$- to $C_4$-alkyl, COCL or phenyl, or
$R_1$ and $R_2$ together are

8. The process according to claim 6, in which
$R_3$ is H, $C_1$- to $C_4$-alkyl, CO-O-$C_1$- to $C_4$-alkyl, CN or phenyl,
$R_4$ is $C_1$- to $C_4$-alkyl or phenyl,
X is Cl, Br, O—$C_1$- to $C_4$-alkyl or S—$C_1$- to $C_4$-alkyl, and
Y is Cl or Br.

9. The process according to claim 6, wherein the solvent in reaction step (a) is water, an alcohol, acetonitrile, dimethylformamide or a mixture thereof, the condensing agent is a basic compound employed in 1 to 3 times the molar amount of the carbonyl-containing compound, and the reaction is carried out at a temperature from 20° to 150° C.

10. The process according to claim 6, wherein the benzodioxenone in reaction step (b) is reacted with 1 to 1.5 times its molar amount of phosphorus pentachloride at 50° to 240° C.

11. The process according to claim 6, wherein the dichlorobenzodioxene in reaction step (c) is reacted at −10° to +120° C. with 2 to 15 times its molar amount of a fluorinating agent selected from the group consisting of hydrogen fluoride, antimony trifluoride, potassium fluoride and sodium fluoride.

12. The process according to claim 7, in which
$R_3$ is H, $C_1$- to $C_4$-alkyl, CO—O—$C_1$ to $C_4$-alkyl, CN or phenyl,
$R_4$ is $C_1$- to $C_4$-alkyl or phenyl,
X is Cl, Br, O—$C_1$ to $C_4$-alkyl or S—$C_1$ to $C_4$-alkyl, and Y is Cl or Br,
the solvent in reaction step (a) is water, an alcohol, acetonitrile, dimethylformamide or a mixture thereof, the condensing agent is a basic compound employed in 1 to 3 times the molar amount of the carbonyl-containing compound, and the reaction is carried out at a temperature from 20° to 150° C., the benzodioxenone in reaction step (b) is reacted with 1 to 1.5 times its molar amount of phosphorus pentachloride at 50° to 240° C., and the dichlorobenzodioxene in reaction step (c) is reacted at −10° to +120° C. with 2 to 15 times its molar amount of a fluorinating agent selected from the group consisting of hydrogen fluoride, antimony trifluoride, potassium fluoride and sodium fluoride.

13. A process for producing a compound of the formula

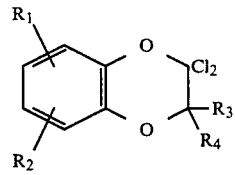

in which
$R_1$ and $R_2$ each independently is H, F, Cl, Br, COF, COCl, CO—O-alkyl, CN, alkyl, $NO_2$, $SO_2F$, $SO_2Cl$, $OCF_3$, $OCF_2Cl$, $SCF_3$, $CF_3$, $SCF_2Cl$, phenyl, substituted phenyl, O-alkyl, O-aryl, S-alkyl or S-aryl, or
$R_1$ and $R_2$ together are
$R_3$ is H, alkyl, aryl, CO—O-alkyl, CN, substituted alkyl or substituted aryl, and
$R_4$ is alkyl, aryl, CO—O-alkyl, CN, substituted alkyl or substituted aryl,
which comprises reacting a benzodioxenone of the formula

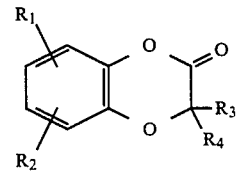

with phosphorus pentachloride.

* * * * *

UNITED STATES PATENT AND TRADEMARK OFFICE
CERTIFICATE OF CORRECTION

PATENT NO. : 4,681,955

DATED : July 21, 1987

INVENTOR(S) : Albrecht Marhold

It is certified that error appears in the above-identified patent and that said Letters Patent is hereby corrected as shown below:

Col. 2, line 23         After "NO$_2$," insert --SO$_2$F,--

Col. 5, line 18         Before "120°" insert -- + --

Col. 6, Table 1, last column, line 5 under heading         Delete "19 mbar" and substitute --18 mbar--

Signed and Sealed this

Third Day of May, 1988

Attest:

Attesting Officer

DONALD J. QUIGG

Commissioner of Patents and Trademarks